US012203878B2

(12) United States Patent
Porsch et al.

(10) Patent No.: US 12,203,878 B2
(45) Date of Patent: Jan. 21, 2025

(54) METHOD FOR MONITORING AND/OR CALIBRATING A DEVICE DESIGNED FOR THE THREE-DIMENSIONAL X-RAY OPTICAL INSPECTION OF SEEDLINGS IN DIFFERENT GROWTH PHASES

(71) Applicants: Fraunhofer-Gesellschaft zur Förderung der Angewandten Forschung e.V, Munich (DE); Strube D&S GmbH, Söllingen (DE)

(72) Inventors: Felix Porsch, Saarbrücken (DE); Antje Wolff, Söllingen (DE); Andreas Gelz, Saarbrücken (DE); Yvonne Götz, Söllingen (DE); Marc Neuhoff, Söllingen (DE)

(73) Assignees: Antje Wolff, Söllingen (DE); Fraunhofer-Gesellschaft zur Forderung der Angewandten Forschung e.V., Munich (DE); Strube D&S GmbH, Söllingen (DE)

( * ) Notice: Subject to any disclaimer, the term of this patent is extended or adjusted under 35 U.S.C. 154(b) by 231 days.

(21) Appl. No.: 17/813,943

(22) Filed: Jul. 21, 2022

(65) Prior Publication Data
US 2023/0023519 A1    Jan. 26, 2023

(30) Foreign Application Priority Data
Jul. 23, 2021   (DE) .................. 10 2021 207 924.5

(51) Int. Cl.
*G01N 23/046*     (2018.01)
*G01N 23/18*      (2018.01)
*G01N 33/00*      (2006.01)

(52) U.S. Cl.
CPC ........... *G01N 23/046* (2013.01); *G01N 23/18* (2013.01); *G01N 33/0098* (2013.01)

(58) Field of Classification Search
None
See application file for complete search history.

(56) References Cited

U.S. PATENT DOCUMENTS 5,864,984 A * 2/1999 McNertney ............. A01C 1/025
382/110
7,367,155 B2 * 5/2008 Kotyk ................... B01L 3/5085
47/14
7,838,437 B2 * 11/2010 Reber ..................... H01L 31/04
438/564
8,935,881 B2 * 1/2015 Wolff ..................... A01C 1/025
47/14
8,941,062 B2 * 1/2015 Wagner .............. G01N 15/1492
250/338.5
10,519,206 B2 * 12/2019 Noelke .................... C12N 1/12
10,709,073 B2 * 7/2020 Millar ....................... A01G 9/24
10,951,831 B2 * 3/2021 Seiffert ................... H04N 23/72
11,588,979 B2 * 2/2023 Seiffert .................... G01N 21/27
2011/0186121 A1 * 8/2011 Horteis ........... H01L 31/022425
252/512
2013/0000194 A1 * 1/2013 Wolff ..................... A01C 1/025
702/19
2013/0008085 A1 * 1/2013 Aikala ..................... A01C 1/00
250/492.1
2013/0126399 A1 * 5/2013 Wolff ..................... B07C 5/342
209/555
2015/0223403 A1 * 8/2015 Aikala ................... A01H 4/008
250/492.1
2017/0283473 A1 * 10/2017 Noelke .............. C12N 15/8261

FOREIGN PATENT DOCUMENTS

| CN | 106248700 A |   | 12/2016 |              |
|----|-------------|---|---------|--------------|
| CN | 106709986 A |   | 5/2017  |              |
| CN | 106248700 B | * | 11/2019 | ... G01N 23/046 |
| CN | 106709986 B | * | 6/2020  |              |

OTHER PUBLICATIONS

English Translation of CN 106709986 B (Year: 2020).*
English Translation of CN 106248700 B (Year: 2019).*

(Continued)

*Primary Examiner* — Marcus H Taningco
*Assistant Examiner* — Djura Malevic
(74) *Attorney, Agent, or Firm* — Marshall & Melhorn, LLC

(57) ABSTRACT

A method for monitoring and/or calibrating a device designed for three-dimensional X-ray optical inspection of seedlings in different growth phases may optically or X-ray optically measure natural seedlings in three dimensions at predetermined times during their growth phase. The method may create a control program for a device which is designed for the three-dimensional printing of artificial seedlings as reference samples which are replicas of the natural seedlings in each case using the recorded measured values. The method may also produce artificial seedlings with a plastic using the device in accordance with the created control program. The artificial seedlings thus produced may be measured three-dimensionally by X-ray optics and the measured values thus acquired may be recorded in a control chart or an already created control chart is adapted, with which control chart monitoring and/or calibration of the device designed for the three-dimensional X-ray optical inspection of seedlings is performed.

5 Claims, No Drawings

(56) References Cited

OTHER PUBLICATIONS

German Patent and Trademark Office, German Examination Report in Application No. DE 10 2021 207 924.5, dated Dec. 4, 2021, 8 pages, München, Germany.

Liang, T. et al., Small-scale modelling of plant root system using 3D printing, with applications to investigate the role of vegetation on earthquake-induced landslides, Landslides, Mar. 7, 2017, 1747-2765.

Mallett, S.D. et al., Additive manufacturing and computed tomography of bio-inspired anchorage systems, Geotechnique Letters 8, Sep. 2018, 219-225.

* cited by examiner

METHOD FOR MONITORING AND/OR CALIBRATING A DEVICE DESIGNED FOR THE THREE-DIMENSIONAL X-RAY OPTICAL INSPECTION OF SEEDLINGS IN DIFFERENT GROWTH PHASES

FIELD

The invention relates to a method for monitoring and/or calibrating a device designed for three-dimensional X-ray optical inspection of seedlings in different growth phases.

BACKGROUND

Increasingly, modern techniques are finding their way into the rather conservative field of agricultural engineering. This includes the use of computed tomography (CT) for quality control in seed production.

Quality control also includes regular checks of the respective test device itself. A common method for doing so is to use reference samples and control charts. The reference samples are regularly tested with the test device and the measurement results are entered in the control chart. In this way, systematic changes in measured values that occur over time can be detected and corrective measures can be taken if necessary.

An essential prerequisite for this is that the respective reference sample itself does not change over time. This method has already been used successfully for many years in the testing of sugar beet seeds using computed tomography.

A new application of CT for quality assurance in seed production is its use for assessing the germination capacity and germinating power of seedlings. In so-called germination tests, the growing seedlings are tomographed several times at intervals of days and the CT images are evaluated using digital image processing.

In this application, however, no seedlings can be used as a reference sample, as these are constantly changing and also do not have a long shelf life.

In order to nevertheless achieve a certain level of quality assurance, various process parameters are constantly monitored. These include, for example, the operating values of the X-ray tube or the edge definition in the CT reconstruction.

However, this does not exclude the possibility that undetected disturbance variables influence the result. Also, the influence of disturbance variables on the final result of the evaluation is difficult to estimate, since the relationship between the radiographic image, the CT reconstruction and the image evaluation is only indirect and very complex.

Quality control charts can therefore not be created using this method.

SUMMARY

It is therefore the object of the invention to provide means by which the monitoring and/or calibration of test device or devices with which a three-dimensional X-ray optical inspection of seedlings can be improved, the accuracy increased and comparable results obtained on a wide variety of seedlings.

In accordance with the invention, this object is achieved by a method having the features of the claims. Advantageous embodiments and further developments of the invention can be realized with features designated in dependent claims.

The method involves the three-dimensional optical or X-ray measurement of natural seedlings at specified times during their growth phase. A control program for a device which is designed for the three-dimensional printing of artificial seedlings as reference samples which are replicas of the natural seedlings is created in each case using the recorded measured values. The artificial seedlings to be produced with the correspondingly created control programs are made of a plastic.

The artificial seedlings produced in this way are then measured in three dimensions by X-ray. The measured values recorded in this process are entered in a control chart or an already created control chart is adapted accordingly. The control chart is used to monitor and/or calibrate the equipment designed for three-dimensional X-ray optical inspection of seedlings (in particular a computer tomograph).

With the device designed for three-dimensional printing, the respective plastic can be processed dropwise or by means of filaments, in the case of so-called fused filament fabrication (FFF) or by means of stereolithography, in order to produce artificial seedlings that have a dimensioning and geometric shape that correspond to natural seedlings in various predefinable growth phases.

With the optically or X-ray optically recorded three-dimensional measured values of natural germs, a CAD control program can be created in each case in order to control the device for printing accordingly.

In this way, artificial seedlings can be produced that correspond to typical growth phases for a particular plant species. This can be the case, for example, when a first shoot has formed, at least a predeterminable number of shoots have formed, or shoots have reached a certain size.

For printing, a plastic should be used that has an X-ray absorption value that deviates by a maximum of ±50%, preferably a maximum of 30%, from X-ray absorption values of natural seedlings. Deviations in the direction of higher X-ray absorption can be better tolerated than would be the case with lower absorption values. The above plus/minus values should therefore rather be evaluated as a maximum of 50% or preferably a maximum of 30%.

For this purpose, additives can also be added to a polymeric plastic with which an improved adaptation of the X-ray absorption values can be achieved.

The invention can circumvent the problem of poor shelf life of seedlings.

It is possible to print even the finest structures down to the order of tenths of millimeters. Many critical features of a seedling, such as roots, leaves, stem or seed remains can be specifically reproduced and also modified, in particular to be able to reproduce typical anomalies of seedlings.

After printing artificial seedlings, processing can be performed on the artificial seedlings to expose or straighten contour elements present on the surface of a seedling. Excess plastic can be removed mechanically or thermally, e.g. by means of laser radiation, or contour elements such as shoots or leaves can be bent up.

The artificial seedlings produced can then be placed in the same germination vessels and with the same substrates as used in the germination tests with natural seedlings. This allows these artificial seedlings to undergo the same testing process as in seedling testing with natural seedlings and the measurement results to be entered in a control chart.

The main advantage over the previous solutions is that a real quality control of an X-ray tomographic inspection device with control chart can be performed.

The invention claimed is:

1. A method for monitoring and/or calibrating a device designed for three-dimensional X-ray optical inspection of seedlings in different growth phases, comprising:
   optically or X-ray optically measuring natural seedlings in three dimensions at predetermined times during their growth phase;
   creating a control program for a device which is designed for the three-dimensional printing of artificial seedlings as reference samples which are replicas of the natural seedlings in each case using the recorded measured values, and
   producing artificial seedlings with a plastic using the device in accordance with the created control program,
   wherein the artificial seedlings thus produced are measured three-dimensionally by X-ray optics and the measured values thus acquired are recorded in a control chart or an already created control chart is adapted, with which control chart monitoring and/or calibration of the device designed for the three-dimensional X-ray optical inspection of seedlings is performed.

2. The method according to claim 1, wherein for printing, a plastic is used, the X-ray absorption value of which deviates by a maximum of ±50% from X-ray absorption values of natural seedlings.

3. The method according to claim 1, wherein after printing artificial seedlings, processing is performed on the artificial seedlings in which contour elements present on the surface of a seedling are exposed or raised.

4. The method according to claim 1, wherein typical anomalies occurring on natural seedlings are reproduced during printing.

5. The method according to claim 1, wherein a computer tomograph is used as a device adapted for three-dimensional X-ray optical inspection of seedlings.

* * * * *